United States Patent [19]

Buckberg et al.

[11] Patent Number: 5,013,296
[45] Date of Patent: May 7, 1991

[54] ANTEGRADE CARDIOPLEGIA CANNULA

[75] Inventors: Gerald D. Buckberg, Los Angeles, Calif.; Robert J. Todd, Salt Lake City, Utah

[73] Assignee: Research Medical, Inc., Salt Lake City, Utah

[21] Appl. No.: 470,702

[22] Filed: Sep. 21, 1989

[51] Int. Cl.⁵ .............................................. A61M 3/00
[52] U.S. Cl. ...................................... 604/44; 604/35; 604/118; 604/164
[58] Field of Search ................. 604/27, 31, 35, 43–45, 604/52–53, 65, 113, 118, 164–166, 280

[56] References Cited

U.S. PATENT DOCUMENTS

| | | | |
|---|---|---|---|
| 2,538,215 | 1/1951 | Stack | 128/227 |
| 2,669,233 | 2/1954 | Friend | 128/251 |
| 3,678,959 | 7/1972 | Liposky | 137/625.11 |
| 3,859,985 | 1/1975 | Eckhart | 128/2.05 R |
| 4,210,478 | 7/1980 | Shoney | 156/242 |
| 4,249,923 | 2/1981 | Walda | 62/394 |
| 4,397,335 | 8/1983 | Doblar et al. | 137/625.19 |
| 4,413,989 | 11/1983 | Schjeldahl et al. | 604/96 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |
| 4,459,977 | 7/1984 | Pizon et al. | 128/1 |
| 4,512,163 | 4/1985 | Wells et al. | 62/394 |
| 4,529,397 | 7/1985 | Hennemuth et al. | 604/4 |
| 4,531,935 | 7/1985 | Berryessa | 604/45 |
| 4,566,480 | 1/1986 | Parham | 137/271 |
| 4,568,330 | 2/1986 | Kujawski et al. | 604/53 |
| 4,596,552 | 6/1986 | DeVries | 604/35 |
| 4,610,661 | 9/1986 | Possis et al. | 604/52 |
| 4,668,215 | 5/1987 | Allgood | 604/30 |
| 4,689,041 | 8/1987 | Corday et al. | 604/53 |
| 4,714,460 | 12/1987 | Calderon | 604/28 |
| 4,753,637 | 6/1988 | Horneffer | 604/53 |
| 4,804,358 | 2/1989 | Karcher et al. | 600/17 |
| 4,867,742 | 9/1989 | Calderon | 604/35 |
| 4,883,459 | 11/1989 | Calderon | 604/35 |

FOREIGN PATENT DOCUMENTS 0249338 12/1987 European Pat. Off.

OTHER PUBLICATIONS

Charles C. Reed, Diane K. Clark, "Cannulation", Chapter 19, Myocardial Protection, Chapter 23, Cardiopulmonary Perfusion, Texas Medical Press, Inc., Houston, Texas 1975.

Dr. Dwight C. McGoon, "Coronary Perfusion", Journal of Thoracic and Cardiovascular Surgery, vol. 70, No. 6, p. 1025, Dec. 1975.

D. Glenn Pennington, "Direct Coronary Ostial Perfusion", Myocardial Protection in Cardiac Surgery, edited by Arthur J. Roberts, published by Marcel Dekker Corp., pp. 229–250, (date unknown).

Donald G. Mulder et al., "Myocardial Protection During Aortic Valve Replacement", The Annals of Thoracic Surgery, vol. 21, No. 2, Feb. 1976, pp. 123–130.

Jorge Solorzano, M.D. et al., "Retrograde Coronary Sinus Perfusion for Myocardial Protection During Cardiopulmonary Bypass", The Annals of Thoracic Surgery, vol. 25, No. 3, Mar. 1978, pp. 201–208.

(List continued on next page.)

Primary Examiner—Stephen C. Pellegrino
Assistant Examiner—Michael Rafa
Attorney, Agent, or Firm—Workman, Nydegger & Jensen

[57] ABSTRACT

A cannula adapted for antegrade administration of cardioplegic solutions during surgical procedures on the heart. The cannula includes a flow lumen having a smooth interior surface to reduce hemolysis when blood is passed therethrough during reperfusion. Structures are included to allow the wall of the vessel, generally the aortic root, to be readily pierced so that fluid may pass through the flow lumen of the cannula into the heart. A suture flange is provided to secure the cannula to the heart. A pressure lumen is provided to communicate the pressure within the heart to a location where it can be monitored. A vent line is also provided to allow a surgeon to readily vent fluids out of the heart.

31 Claims, 3 Drawing Sheets

OTHER PUBLICATIONS

Philippe Menasche et al., "Retrograde Coronary Sinus Perfusion", Roberts Textbook *Myocardial Protection in Cardiac Surgery*, printed 1987, Chapter 15, pp. 251-262.

Philippe Mensasche, M.D., et al., "Retrograde Coronary Sinus Perfusion: A Safe Alternative for Ensuring Cardioplegic Delivery in Aortic Valve Surgery", *The Annals of Thoracic Surgery*, vol. 34, No. 6, Dec. 1982, pp. 647-658.

Gerald D. Buckberg, M. D., "Strategies and Logic of Cardioplegic Delivery to Prevent, Avoid, and Reverse Ischemic and Reprefusion Damage", *The Journal of Thoracic and Cardiovascular Surgery*, 1987; vol. 93; pp. 127-139.

Gerald D. Buckberg, M.D., "Retrograde Pulmonary Venous Pressure Measurement-Fact or Antifact?", No. 3, pp. 393-405, Mar. 1970.

John W. Kirklin, M.D., et al., "Prevention of Myocardial Damage During Cardiac Operations", *The New England Journal of Medicine*, vol. 301, No. 3, pp. 135-141, Jul. 19, 1979.

Harold V. Liddle and Richard Berryessa, "Metabolic Management of the Myocardium During Cardiac Surgery," *Blades Surgical Diseases of the Chest*, Chapter 23, pp. 649-671, published data unknown, publisher unknown.

International Working Group on Coronary Sinus Interventions, Newsletter, vol. 1, No. 3, Oct. 1987.

Gerald D. Buckberg, M.D., article covering the background of the use of antegrade/retrograde cardioplegic in the combination submitted to the *Journal of Thoracic and Cardiovascular Surgery*, date unknown.

Picture illustrating use of a myocardial cannula during surgery, date and source unknown (possibly from Roberts text).

A sales description of Mayo cannula from the V. Mueller Co. catalog, date unknown.

ANTEGRADE CARDIOPLEGIA CANNULA

BACKGROUND

1. The Field of the Invention

The present invention relates generally to devices used to induce cardioplegia during surgical procedures on the heart. More particularly, the present invention is directed to a cannula used to administer cardioplegic solutions and other liquids into the heart in an antegrade direction with maximum effectiveness and minimum tissue damage.

2. Related Applications

U.S. patent application Ser. No. 187,230, filed Apr. 28, 1989, entitled Retrograde Venous Cardioplegia Catheters and Methods of Use and Manufacture naming Gerald D. Buckberg and Robert J. Todd as joint inventors and U.S. patent application Ser. No. 07/406,382, filed Sept. 12, 1989, entitled Cardioplegia Three-way Double Stopcock naming Robert J. Todd, Douglas L. Smith, and Michael N. Kelly as joint inventors, are now incorporated herein by reference in their entireties.

3. The Background Art

Since the early days of cardiac surgery, it has been recognized that in order to provide optimum surgical conditions when operating on the heart, it is necessary to reasons, an arrested, flaccid heart is preferred during a cardiac surgical procedure over a beating heart with blood flowing through it. Thus, in order to be able to efficiently perform cardiac surgery, it is often necessary to use cardiopulmonary-bypass techniques and to isolate the heart from its life-giving blood supply.

Research has shown that many deaths occurring after cardiac surgery were due to acute cardiac failure. At first, it was believed that the heart was simply beyond repair and that the operation had failed to correct the problem. Later, it was discovered that many of these postoperative deaths were due to new, and often extensive, perioperative (during or within 24 hours after the surgical procedure) myocardial necrosis (death of the heart tissue). Furthermore, many patients who survived were found to have suffered myocardial necrosis to a significant degree as a result of the surgical procedure, thereby resulting in low cardiac blood output.

It is now widely accepted that myocardial necrosis occurs because the energy supply or reserve of the cardiac muscle cells is inadequate to supply the needs of the heart during a surgical procedure where the normal operation of the heart has been interrupted. The availability of oxygen dramatically affects a cell's ability to satisfy these energy requirements.

For example, anaerobic metabolism of glucose produces two (2) moles of adenosine triphosphate ("ATP") per mole of glucose (as well as harmful acid metabolites), whereas aerobic metabolism of glucose produces thirty-six (36) moles of ATP per mole of glucose. This and other facts make it clear that continued cardiac activity during periods of decreased oxygen availability is extremely detrimental to the heart muscle. Therefore, one of the primary goals of myocardial preservation techniques during surgery is to reduce myocardial oxygen consumption.

Myocardial oxygen consumption is significantly reduced by stopping the electromechanical work of the heart. The oxygen demands of the beating empty heart at 37° C. are four to five times those of the arrested heart (i.e., 4–5 ml/100-gm/min compared with 1 ml/100-gm/min). Buckberg, G. D., "Strategies and Logic of Cardioplegic Delivery to Prevent, Avoid, and Reverse Ischemic and Reperfusion Damage," 93 *The Journal of Thoracic and Cardiovascular Surgery*, 127, 136 (January 1987) (hereinafter referred to as: Buckberg, "Strategies and Logic of Cardioplegic Delivery").

Oxygen consumption can be reduced further by cooling the heart. For example, the oxygen requirements of the arrested heart at 20° C. are 0.3 ml/100-gm/min and are reduced to only 0.15 ml/100-gm/min at 10° C. On the other hand, the oxygen requirements of the beating or fibrillating heart at comparable temperatures, are 2–3 ml/100-gm/min. Buckberg, "Strategies and Logic of Cardioplegic Delivery" at 129.

The normal heart receives its blood supply through the left and right coronary arteries which branch directly from the aorta. Generally, the veins draining the heart flow into the coronary sinus which empties directly into the right atrium. A few veins, known as thebesian veins, open directly into the atria or ventricles of the heart.

A method which has been developed to preserve the health of the myocardium during surgery, and is now widely practiced, is the infusion of a cold cardioplegic fluid to cool the heart while at the same time stop the beating of the heart. After the initial infusion of cardioplegic solution to arrest the heart, the heart is again perfused with cold cardioplegic fluid approximately every thirty (30) minutes to maintain the cool, dormant state of the heart.

The use of cardioplegia to protect the myocardium has proven the most advantageous protective measure of those used to date. Cardioplegia, which literally means "heart stop," may be administered in an antegrade manner (through arteries, such as the aorta, in the normal direction of blood flow), in a retrograde manner (through veins, such as the coronary sinus, in opposition to the normal blood flow direction), or in a combination of retrograde and antegrade administration. Cardioplegic solutions, typically containing potassium, magnesium procaine, or a hypocalcemic solution, stop the heart by depolarizing cell membranes.

Cardioplegia may be induced immediately after extracorporeal circulation has begun, provided that the pulmonary artery is collapsed to attest to the adequacy of venous return. In antegrade cardioplegia, extracorporeal circulation is begun by inserting a single venous, return catheter into the right atrium to transfer blood from the body to the heart-lung machine which pumps the blood into the aorta above an aortic clamp.

After it is determined that venous return is adequate, a cannula is then inserted into the aorta beneath the clamp through which the cardioplegic solution is administered. The cardioplegic solution flows through the coronary arteries in the normal blood flow direction. As mentioned, cardioplegic solution is periodically administered to the heart throughout the surgical procedure.

When it is time to resume the normal function of the heart, one method to resuscitate the heart requires the use of warmed blood introduced into the heart through the antegrade cardioplegia cannula to reperfuse the heart. The use of warmed oxygenated blood as the reperfusion solution has been recognized as reducing damage to the heart. Buckberg, "Strategies and Logic of Cardioplegic Delivery" at 134. Thus, the antegrade cardioplegia cannula must be fabricated so that the blood cells do not experience damage (hemolysis) during their passage through the cannula. Cannulas having obstructions to fluid flow may cause hemolysis as the blood cells negotiate sharp corners and encounter turbulence as they pass through the fluid carrying lumen of the apparatus.

In view of the problems and needs present in the art, it would be an advance in the art to provide an apparatus for performing antegrade cardioplegia more efficiently and with less tissue damage than possible with previous apparatus. It would be another advance in the art to provide a cannula specifically adapted for performing antegrade cardioplegia which reduces the possibility of hemolysis during reperfusion. It would be a still further advance in the art to provide an antegrade cardioplegia cannula which is reliably and economically constructed.

BRIEF SUMMARY AND OBJECTS OF THE INVENTION

The present invention is an apparatus specifically designed for performing antegrade cardioplegia on the human heart during surgical procedures involving the heart. The embodiments of the invention include a cannula which perform several principal functions including: introduction of cardioplegic solutions and other liquids into the heart; communication of the pressure within the heart to a point where it can be monitored by medical equipment adapted for monitoring such pressures; and, venting fluids from the heart.

The embodiments of the present invention include a flow lumen adapted for passing cardioplegic solutions and other liquids into the heart. A means for piercing is also provided to allow the embodiment to readily pierce the vessel wall of aortic root vessel which is the preferred site for performing antegrade cardioplegia.

The means for piercing includes a sharpened stiffening stylet which extends out of the end of the cannula and assists with carrying out the piercing function. The stylet is removed after insertion of the cannula. Also provided is a connecting means for connecting the flow lumen to a liquid reservoir, generally a reservoir of cardioplegic solution. Also included is a pressure lumen or pressure line. The pressure line is connected to a pressure port which opens into the heart vessel, generally the aortic root. The connection of the pressure line to the pressure port allows the pressure within the vessel, e.g., the aortic root, to be communicated through the pressure lumen to a medical device adapted for pressure monitoring.

The embodiments of the present invention may also include a vent line. The vent line intersects the flow lumen and functions to allow a surgeon to vent fluids from the heart. A suture flange, or other structure performing a similar function, is included to serve as a means for securing the cannula to the heart.

In view of the problems and needs experienced in the art, it is an object of the present invention to provide an apparatus for efficiently carrying out antegrade cardioplegia. It is a further object of the present invention to provide a cannula specifically adapted for performing antegrade cardioplegia which reduces the occurrence of hemolysis when blood is passed therethrough.

It is still another object of the present invention to provide a antegrade cardioplegia cannula which provides structures for supplying cardioplegic solutions and other fluids to the heart, for monitoring of the internal pressure within the heart vessel, and for venting fluids out of the heart. It is a still further object of the present invention to provide a antegrade cardioplegia cannula which is reliably and economically constructed.

These and other objects and features of the present invention will become more fully apparent from the following description and appended claims taken in conjunction with the accompanying drawings.

DETAILED DESCRIPTION OF THE PREFERRED EMBODIMENT

Reference will now be made to the drawings wherein like parts are designated with like numerals throughout. Also, as used herein, the term "fluid" is intended to include both liquids and gases. Those skilled in the pertinent arts will readily realize whether a liquid, gas, or both, is intended by the context of the term.

Furthermore, as used herein, the term "heart" is intended to include within its meaning the heart and those structures associated with the heart, for example, the aortic root. Moreover, the term "vessel" will be used to refer to the blood vessels associated with the heart, such as the aortic root, as well as any other insertion site a surgeon may choose to administer cardioplegia using an embodiment of the present invention.

The aortic root is the most common site for administering cardioplegic solutions in an antegrade direction. Thus, the embodiment of the present invention will be described using the aortic root as the insertion site, however, the present invention may be used at other insertion sites.

Figure 1:
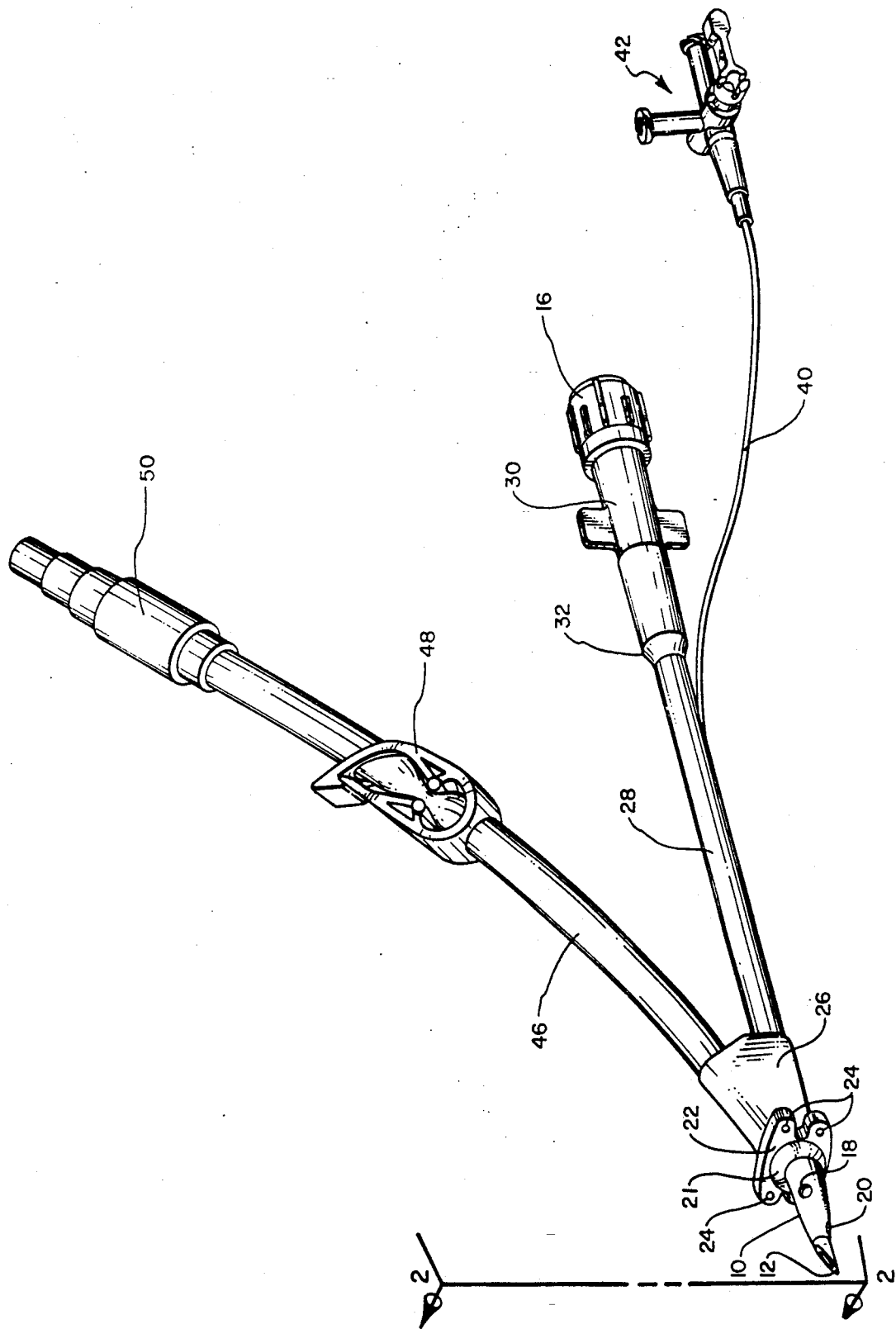
FIG. 1 is a perspective view of the presently preferred embodiment of the antegrade cardioplegia cannula of the present invention.

Provided in FIG. 1 is a perspective view of the presently preferred antegrade cardioplegia cannula of the present invention. Each of the structures which allows the cannula to carry out the functions of: (1) introducing cardioplegic solutions and other liquids into the heart; (2) communicating the pressure within the heart to a point where it can be monitored by equipment adapted for monitoring such pressure; and, (3) venting fluids from the heart will each be explained below.

Reference will now be made to FIG. 1 which is a perspective view of the presently preferred embodiment of the present invention. In order to allow the surgeon to insert the cannula illustrated in FIG. 1 into the heart, a means for piercing is provided. As explained, when antegrade cardioplegia is performed, the cannula is generally inserted into the aortic root but the present invention may be used at other insertion sites if desired by the surgeon.

The illustrated cannula provides one example of a means for piercing. As shown best in FIG. 1, the sharpened tip of a stylet shown at 12 protrudes out of the cannula. Also shown in FIG. 1 is the tapered distal end 10 of a flow lumen body 28.

Together, stylet tip 12 and tapered flow lumen body 10 function to pierce the vessel wall during insertion of the illustrated embodiment. The illustrated structures greatly facilitate the insertion of the cannula through the aortic root vessel wall or the wall of another vessel associated with the heart. Those skilled in the art, however, will appreciate that other structures may be used as a means for piercing using the teachings contained herein.

Also illustrated in FIG. 1 is a suture flange 22. In the illustrated embodiment, suture flange 22 is provided with a plurality of bores which are represented at 24. Bores 24, however, are optional and may be omitted if desired.

Suture flange 22 is used by the surgeon to attach the cannula to the heart so that the cannula will remain in position while administering cardioplegia. Suture flange 22 is exemplary of the structures which may be used to function as the securing means of the present invention. It is to be understood that structures other than the illustrated suture flange may function as a securing means within the scope of the present invention.

Figure 2:
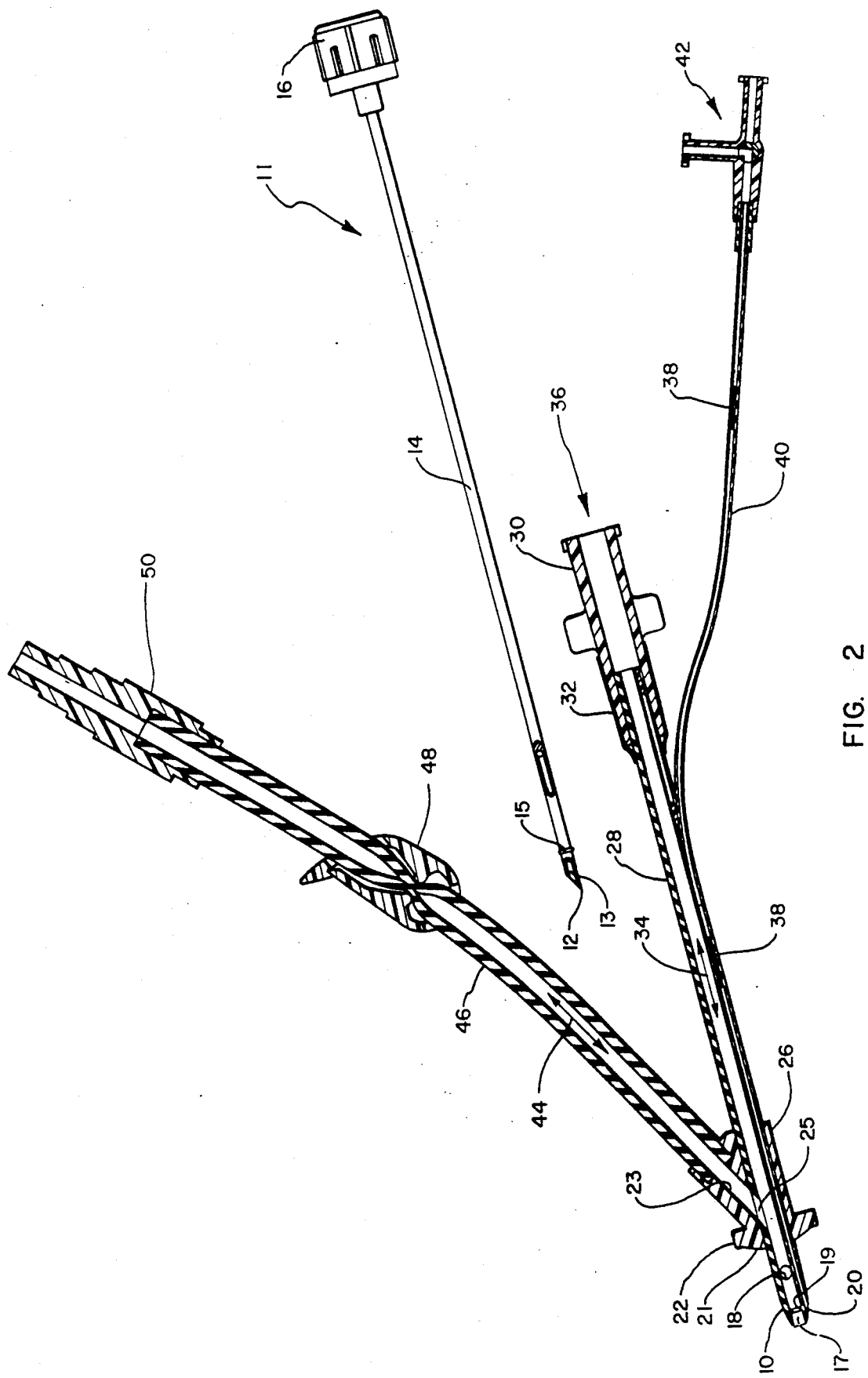
FIG. 2 is an elevated cross sectional view of the antegrade cardioplegia cannula illustrated in FIG. 1.

As represented in both FIGS. 1 and 2, suture flange 24 is formed integrally with cannula hub 26. As with all of the structures described herein, the cannula hub 26 may be fabricated from polymer materials well known in the art using fabrication techniques also known to those skilled in the art. Also provided on cannula hub 26 is a ring of tampon-like material 21 which functions to reduce leakage of liquid from the heart at the site of insertion.

Referring now to the cross sectional view of FIG. 2, the internal structure of the cannula can be seen. The passageway provided to administer cardioplegic solutions and other fluids into the heart is formed by the flow lumen body 28 which defines a flow lumen designated by arrows 34 in FIG. 2. Flow lumen body 28, which may also be referred to as a hollow member, is preferably a length of double lumen tubing which defines flow lumen 34 and, as will be explained shortly, a pressure lumen 38 within its external circumference.

Still referring to FIG. 2, provided at the tapered end 10 of flow lumen body 28 is a flow orifice 17 and a flow port 18. Both flow orifice 17 and flow port 18 allow fluid to pass from flow lumen 34 into the heart.

Flow port 18 also functions to allow gases which may be present inside the vessel at the insertion site to escape into the flow lumen where they may be vented by the surgeon using the illustrated embodiment. Since the heart is open to the atmosphere during surgery, gases often accumulate inside the vessel at the insertion site. Thus, flow port 18 is preferably spaced from suture flange 22 a distance which is slightly greater than the thickness of the vessel wall at the insertion site. Furthermore, more than one flow port 18 is provided.

As can be seen best in FIG. 2, flow lumen body 28 is inserted through cannula hub 26 and is fixed into place in the cannula hub. The interior surface of flow lumen 34 is generally smooth and without any obstructions to the flow of fluids.

It is important that the interior of flow lumen 34 be generally smooth since blood cells may be damaged (hemolysis) 22 if they strike sharp corners or objects, or if excessive turbulence is encountered, while passing under pressure through flow lumen 34 into the heart. The use of warmed, oxygenated blood for reperfusion of the heart is a practice with some surgeons in order to reduce reperfusion damage which sometimes otherwise occurs when heart functions are restored while there is yet insufficient oxygen supply available to the heart muscle.

Furthermore, both flow lumen 34 and pressure lumen 38 are preferably fabricated from a transparent material so that any bubbles or obstructions present therein may be readily observed. Also, pressure lumen 38 should have a generally smooth interior surface so that any bubbles or obstructions lodged therein may be easily removed.

In the cannula illustrated in FIG. 2, a threaded luer lock connector 30 is attached to a proximal end of pressure lumen body 28. Also shown in FIG. 2 is a layer of heat shrinkable tubing 32 which is applied to the area where connector 30 and flow lumen body 28 are joined. Tubing 32 is preferably colored red to identify the flow lumen.

As will be appreciated by examining FIG. 2, flow lumen body 28 is preferably fabricated from flexible dual lumen tubing which is made rigid by a stylet 11. The insertion of stylet 11 into flow lumen 34 in the direction shown by arrow 36 greatly facilitates insertion of the cannula into the heart by stiffening the cannula. When stylet 11 is inserted into flow lumen 34, stylet tip 12 protrudes out from flow orifice 17 as represented in FIG. 1.

With stylet 11 inserted into flow lumen 34, stylet 11 is releasably locked into flow lumen body 28. A luer lock cap 16 attached to the end of stylet shaft 14 engages threaded connector 30 provided at the end of flow lumen body 28 and these structures function as a means for releasably locking the stylet into the flow lumen.

Stylet 11 is also provided with a flashback channel 15 having an opening at stylet tip 12 and another opening a short distance up stylet shaft 14. Flashback channel 15 allows blood from the vessel to "flashback" into the cannula as soon as the vessel wall has been penetrated. The presence of blood in the cannula signals to the surgeon that the vessel wall has been pierced.

As seen best in FIG. 2, stylet shaft 14 is provided with an annular ring 15 positioned about its circumference. Also, the interior of flow lumen 38 is provided with a ridge 19 which protrudes slightly into flow lumen 38. When stylet 11 is fully inserted into the flow lumen and locked into place, ridge 19 is distally adjacent to annular ring 15. This structure provides the tapered end of the flow lumen body extra support against collapse while piercing the vessel wall during insertion.

In use, connector 30 is attached to a length of tubing leading to a liquid reservoir supplying cardioplegic solution or some other liquid. When desired by the surgeon, fluid passes under pressure through flow lumen 34, out through flow orifice 17 and flow port 18, and into the heart.

Another important function carried out by the cannula illustrated in the figures is the communicating of the pressure present in the aortic root, or other vessel, to a location where it may be monitored by medical equipment designed to carry out such functions. To perform this function, a pressure port 20, partially shown in FIG. 1, is provided.

Pressure port 20, which is positioned externally to flow orifice 17 and flow port 18, is in contact with the fluid present in the aortic root vessel and the pressure within the vessel is transferred to pressure port 18. During administration of cardioplegia and reperfusion of the heart, a surgeon needs to know the pressure within the vessel to avoid administering the fluids at too high a pressure which may cause serious damage to vital tissues.

Referring now to FIG. 2, the conduit formed by pressure line 38 can be seen extending from pressure port 20 to stopcock 42. For part of its length, pressure lumen 38 comprises a second, smaller lumen formed within the exterior circumference of flow lumen body 28. At a point about two-thirds along the length of flow lumen body 28 a length of pressure lumen tubing 40 intercepts the smaller lumen formed within the flow lumen body 28 and continues the pressure lumen 38 to stopcock 42.

At stopcock 42, the pressure lumen may be connected to a medical device, such as a pressure transducer (not shown in the figures), by a length of tubing as is well known in the art. The fluid column present in the pressure line communicates the pressure from within the vessel to stopcock 42. In this way, a surgeon is able to readily monitor the pressure within the aortic root vessel during administration of cardioplegic solutions and other fluids.

Importantly, the position of pressure port 20 allows the actual pressure within the vessel, such as the aortic root, to be measured rather than the pressure at which the liquids within flow lumen 34 are being infused. If the pressure within the vessel becomes too high, damage will result. Thus, pressure port 20 is positioned outside of flow lumen 34 and flow orifice 17 and in direct contact with the pressure in the vessel such as the aortic root.

It is often the case that a surgeon desires to vent fluids, and particularly gases, out of the heart. As shown best in FIG. 2, vent tube 46 and cannula hub 26 cooperate to define a vent line, designated by arrows 44, whereby fluids may pass out of the heart without interfering with the operation of the flow lumen.

Still referring to FIG. 2, an opening 25 is provided in the wall of flow lumen body 28 aligned with a vent bore 23 provided in cannula hub 26. Vent tube 46 is attached to cannula hub 26 and opening 25 and vent bore 23 places vent line 44 in communication with the interior of the heart by way of flow lumen 34 and its associated structures.

A clamp 48 is provided on vent tubing 46 to close off the vent line unless opened during the surgical procedure. A vent connector 50 is also provided at an end of the vent line to facilitate attaching the vent line to a source of vacuum.

Those skilled in the art will appreciate that structures other than those just illustrated and described may be used to provide a vent line for the cannula of the present invention.

Having described the structure of the illustrated embodiment, the presently preferred method of manufacturing the described structure will now be explained. It is to be understood, however, that other methods of manufacturing may be used within the scope of the present invention.

The illustrated embodiment preferably is fabricated using a double lumen tubing available from any of several commercial suppliers. Once the double lumen tubing has been cut to the proper length, the tapered distal end of the cannula is formed.

The tapered distal end of the cannula is produced by inserting the end of the double lumen tubing into a die. The die may be formed so that the tapered distal end of the cannula is square, as shown in the figures, or if desired the tapered distal end of the cannula may be formed at an angle.

To form the tapered end, the die is induction heated to a temperature sufficiently high enough to heat form the end of the tubing to the desired taper. Two mandrels are included in the die and protrude into the tubing lumens which will serve as the flow lumen and the pressure lumen. The two mandrels serve to keep the lumens from being distorted as the taper is being heat formed.

Preferably, the die used to form the tapered distal end includes water cooling structures so that the temperature of the die may be reduced quickly thus assuring that the proper shape of the tubing and the lumens is not distorted as the tubing is removed from the die. While either polyvinyl chloride or polyurethane tubing may be used, the cooling of the material prior to removal from the die is particularly important when using the preferred polyurethane materials.

After the tapered distal end has been formed, flow port 18 and opening 25 are formed in the flow lumen body. Also, a cut is made into the pressure lumen contained in the flow lumen body and pressure lumen tube 40 is secured in-line therewith. Pressure lumen tube 40 may be solvent bonded in place. Once the pressure lumen tube is secured in place, the ends of the unused portion of the smaller lumen in the flow lumen body is sealed.

Next, cannula hub 26 is positioned on flow lumen body 28 and solvent bonded into place after the vent line portion of the cannula hub has been aligned with opening 25 previously made in flow lumen 34. A clamp 48 is placed on vent tube 46 and the vent tube is then bonded into the cannula hub. The remaining step is to insert stylet 11 into the flow lumen and lock the stylet into place therein.

Figure 3:
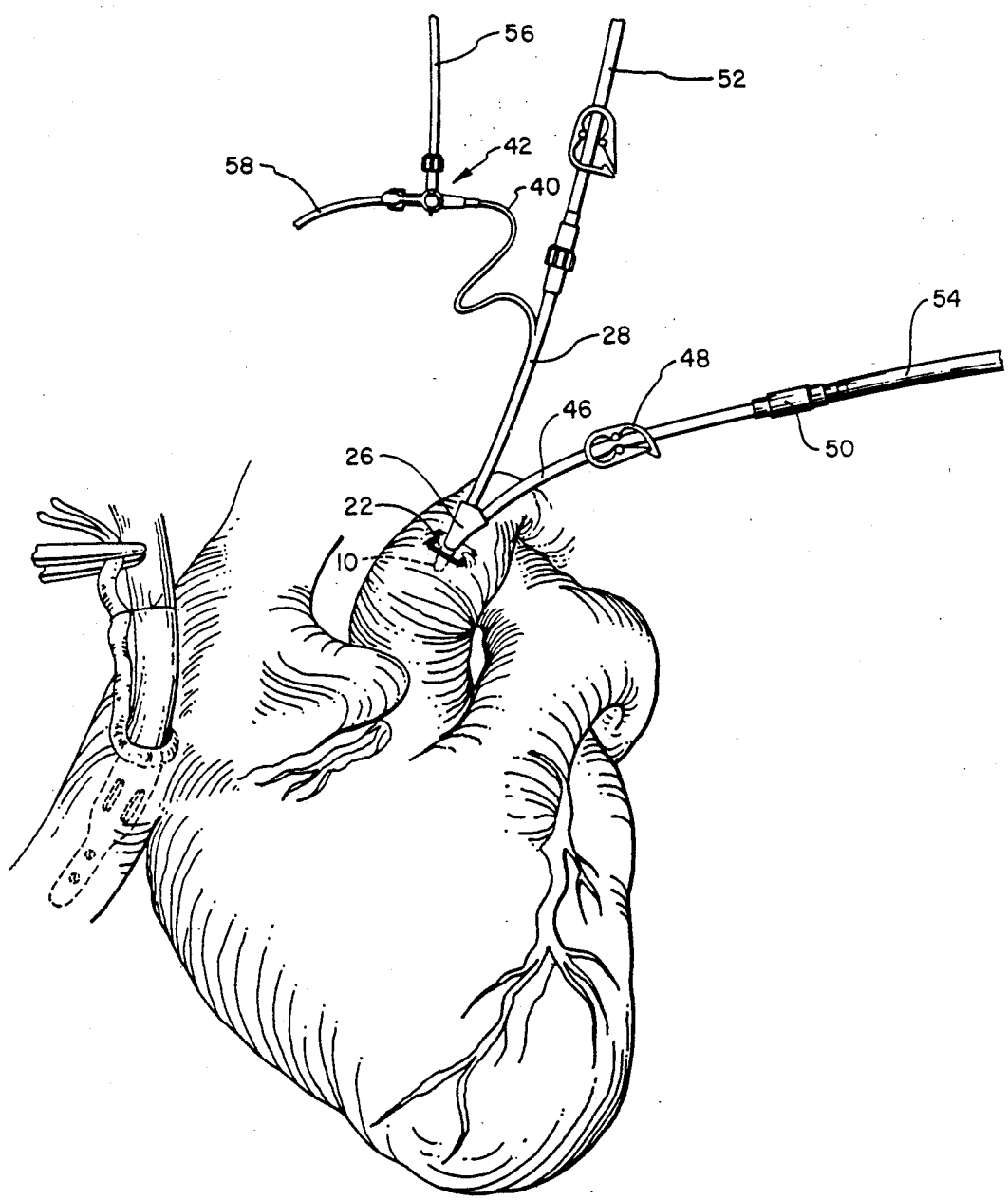
FIG. 3 is a partially cut away perspective view of the antegrade cardioplegia cannula illustrated in FIG. 1 secured to aortic root of the human heart.

FIG. 3 shows the cannula which is illustrated in FIGS. 1 and 2 secured in place on the heart and tapered first end 10 of flow lumen body 28 inserted through the aortic root wall.

Generally, the insertion site for the described cannula will vary little from the commonly used site on the aortic root. Still, under some circumstances other sites may be used, for example, if the aorta is to be replaced.

In use, the aorta is first clamped and extracorporeal circulation is begun. The aorta wall is pierced and the presence of blood in the cannula signals to the surgeon that the distal end of the cannula is within the aortic vessel. The previously described suture flange is used to secure the cannula to the heart and the stylet is removed. Appropriate connections are made to the flow lumen, pressure lumen, and vent line. After the adequacy of extracorporeal circulation has been confirmed, cardioplegic solution is supplied to the flow lumen from a liquid reservoir (not shown) by way of tube 52 and infused into the heart.

Throughout a surgical procedure, cardioplegic solutions are periodically introduced into the heart to maintain cardioplegia. When it is time to restore the function of the heart, blood at body temperature may be infused through the flow lumen to reperfuse the heart. The use of warmed, oxygenated blood as a reperfusate has been found to reduce reperfusion damage.

Shown in FIG. 3 is vent connector 50 attached to a tube 54 which supplies a vacuum to assist in venting the heart during the surgical procedure. As mentioned, gases accumulate within the aorta during the surgery since the heart has been opened to the atmosphere.

Also illustrated in FIG. 3 is stopcock 42 which is attached to tube 58. Tube 58 leads preferably leads to a pressure transducer (not shown) which monitors the pressure present in the aortic vessel. Also attached to stopcock 42 is a tube 56 which leads to a source of sterile liquid used to prime or flush the pressure lumen.

With the cannula of the present invention secured to the heart, the surgeon may introduce cardioplegic solutions and other fluids into the heart when desired by operating clamp 60, monitor the pressure within the vessel as fluid is administered into the heart, and also vent fluids from the heart by operating clamp 48. Once the surgical procedure is completed and the heart has been resuscitated, the cannula is removed in accordance with usual surgical procedures.

It will now be appreciated that the antegrade cardioplegia cannula of the present invention provides an apparatus for performing antegrade cardioplegia more efficiently than possible with previous apparatus. The cannula described herein also reduces the possibility of hemolysis during reperfusion when using blood as a reperfusate. Still further, the antegrade cardioplegia cannula of the present invention is reliably and economically constructed as well as being easier to use than those devices previously available.

It will be appreciated that the apparatus of the present invention is capable of being incorporated in the form of a variety of embodiments, only one of which has been illustrated and described above. The invention may thus be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cannula for administering cardioplegic solutions and other liquids in an antegrade direction into the heart through the wall of a vessel associated with the heart, the cannula comprising:
    means for piercing the vessel wall, said means positioned at a distal end of the cannula;
    a flow lumen having a distal end located adjacent the distal end of the cannula and a proximal end, the flow lumen extending between the means for piercing the vessel wall and a proximal end of the cannula, the flow lumen adapted to be placed in communication with a liquid reservoir and allow the flow of a liquid from the liquid reservoir to the interior of the heart in an antegrade direction;
    first connecting means for connecting the proximal end of the flow lumen to the liquid reservoir;
    a pressure lumen located substantially parallel to the flow lumen having distal and proximal ends;
    a pressure port located at the distal end of the pressure lumen such that the pressure port opens directly into the vessel and does not open into the flow lumen when the cannula is in place on the vessel wall and such that the pressure within the vessel is communicated from the pressure port, through the pressure lumen, to the proximal end of the pressure lumen; and
    second connecting means for connecting the second end of the pressure lumen to a pressure monitoring device.

2. A cannula for administering cardioplegic solutions and other liquids in an antegrade direction into the heart through the wall of a vessel associated with the heart as defined in claim 1 wherein the means for piercing the vessel wall comprises a tapered distal end of the cannula having an orifice at the end thereof and being adapted for piercing the vessel wall, the flow lumen being connected to the orifice.

3. A cannula for administering cardioplegic solutions and other liquids in an antegrade direction into the heart through the wall of a vessel associated with the heart as defined in claim 2 wherein the means for piercing the vessel wall further comprises a removable stylet having a sharpened first end, the stylet being capable of insertion into the flow lumen and extending out of the orifice.

4. A cannula for administering cardioplegic solutions and other liquids in an antegrade direction into the heart through the wall of a vessel associated with the heart as defined in claim 2 wherein the means for piercing the vessel wall further comprises:
    an annular ring positioned on the outer circumference of the stylet; and
    a protrusion positioned on the inner circumference of the distal tapered end of the cannula, the annular ring and the protrusion positioned such that the annular ring is proximally adjacent to the protrusion when the stylet is locked into the flow lumen thereby holding the distal tapered end of the cannula in position as the cannula is inserted through the vessel wall.

5. A cannula for administering cardioplegic solutions and other liquids in an antegrade direction into the heart through the wall of a vessel associated with the heart as defined in claim 2 wherein the stylet further comprises a conduit within the stylet having a first and a second opening, the first opening positioned adjacent the sharpened end of the stylet and the second opening end positioned on the outer circumference of the stylet and remotely from the sharpened end of the stylet.

6. A cannula for administering cardioplegic solutions and other liquids in an antegrade direction into the heart through the wall of a vessel associated with the heart as defined in claim 2 further comprising means for releasably locking the stylet into the flow lumen.

7. A cannula for administering cardioplegic solutions and other liquids in an antegrade direction into the heart through the wall of a vessel associated with the heart as defined in claim 1 wherein the flow lumen comprises a smooth interior surface.

8. A cannula for administering cardioplegic solutions and other liquids in an antegrade direction into the heart through the wall of a vessel associated with the heart as defined in claim 1 wherein the second connecting means comprises a tubing connector.

9. A cannula for administering cardioplegic solutions and other liquids in an antegrade direction into the heart through the wall of a vessel associated with the heart as defined in claim 8 wherein the tubing connector comprises a luer lock connector.

10. A cannula for administering cardioplegic solutions and other liquids in an antegrade direction into the heart through the wall of a vessel associated with the heart as defined in claim 1 wherein the pressure lumen is at least partially formed within the exterior circumference of the flow lumen.

11. A cannula for administering cardioplegic solutions and other liquids in an antegrade direction into the heart through the wall of a vessel associated with the heart as defined in claim 1 wherein the pressure lumen comprises a lumen formed within the exterior circumference of the flow lumen and a length of tubing connected thereto and extending out of the flow lumen.

12. A cannula for administering cardioplegic solutions and other liquids in an antegrade direction into the heart through the wall of a vessel associated with the heart as defined in claim 1 wherein the pressure lumen and the flow lumen each comprise one lumen of a double lumen tube.

13. A cannula for administering cardioplegic solutions and other liquids in an antegrade direction into the heart through the wall of a vessel associated with the heart as defined in claim wherein the pressure port is located outside of the flow lumen.

14. A cannula for administering cardioplegic solutions and other liquids in an antegrade direction into the heart through the wall of a vessel associated with the heart as defined in claim 1 wherein the second connecting means comprises a three way stop cock.

15. A cannula for administering cardioplegic solutions and other liquids in an antegrade direction into the heart through the wall of a vessel associated with the heart as defined in claim 1 further comprising a vent line having first and second ends, the first end of the vent line opening into the flow lumen.

16. A cannula for administering cardioplegic solutions and other liquids in an antegrade direction into the heart through the wall of a vessel associated with the heart as defined in claim 15 further comprising a clamp positioned on the vent line.

17. A cannula for administering cardioplegic solutions and other liquids in an antegrade direction into the heart through the wall of a vessel associated with the heart as defined in claim 15 wherein the vent line comprises a vent connector positioned at its second end.

18. A cannula for administering cardioplegic solutions and other liquids in an antegrade direction into the heart through the wall of a vessel associated with the heart as defined in claim 1 further comprising means for securing the cannula to the vessel wall.

19. A cannula for administering cardioplegic solutions and other liquids in an antegrade direction into the heart through the wall of a vessel associated with the heart as defined in claim 18 wherein the means for securing the cannula to the vessel wall is further for limiting the insertion of the cannula into the vessel.

20. A cannula for administering cardioplegic solutions and other liquids in an antegrade direction into the heart through the wall of a vessel associated with the heart as defined in claim 19 wherein the means for securing the cannula to the vessel wall comprises a suture flange.

21. A cannula for administering cardioplegic solutions and other liquids in an antegrade direction into the heart through the wall of a vessel associated with the heart as defined in claim 19 wherein the means for securing the cannula to the vessel wall comprises a tapered ring encircling the flow lumen and adapted for deforming and plugging the vessel wall at the site of insertion such that liquid leakage from the vessel wall is reduced.

22. An apparatus for infusing liquids into the heart in an antegrade direction, the apparatus comprising:
   a hollow member having a first opening at a distal end and a second opening at a proximal end, the distal end being adapted for piercing a vessel wall which places the first opening in communication with the interior of the vessel and establishes a fluid path from the interior of the vessel to the second opening at the proximal end;
   a first connector located at the proximal end of the hollow member, the first connector being adapted for connecting the hollow member to a source of liquid;
   a removable stylet positioned within the hollow member, the stylet having a first end extending out from the first opening at the distal end of the hollow member said first end of the stylet being sharpened, the hollow member forming a fluid path from the interior to the exterior of the vessel after the stylet has been removed;
   a pressure port positioned externally and adjacent to the first end of the hollow member such that after the first end of the hollow member pierces the vessel wall the port opens into the vessel;
   a pressure conduit having first and second ends, the first end of the conduit being connected to the pressure port;
   a second connector located at the second end of the pressure conduit, the second connector adapted for connecting the pressure conduit to a medical device, the conduit forming a fluid pathway for communicating the pressure present at the pressure port within the vessel to the second connector; and
   a suture flange located near the distal end of the hollow member for securing the apparatus to the vessel wall and for limiting the insertion depth of the apparatus into the vessel, said suture flange including a tapered ring encircling the hollow member and adapted for deforming the vessel wall at the site of insertion such that liquid leakage from the vessel wall is reduced.

23. An apparatus for infusing liquids into the heart in an antegrade direction as defined in claim 22 further comprising means for releasably locking the stylet into the hollow member.

24. An apparatus for infusing liquids into the heart in an antegrade direction as defined in claim 22 wherein the stylet comprises an internal passage extending from its first end to a stylet opening positioned on the side of the stylet remote from its first end.

25. An apparatus for infusing liquids into the heart in an antegrade direction as defined in claim 22 wherein the stylet comprises an annular ring provided on its circumference and adapted for engaging the interior surface of the hollow member adjacent to the first opening.

26. An apparatus for infusing liquids into the heart in an antegrade direction as defined in claim 22 wherein the interior of the hollow member comprises a smooth surface.

27. An apparatus for infusing liquids into the heart in an antegrade direction as defined in claim 22 wherein the pressure conduit comprises a lumen formed within the external circumference of the hollow member.

28. An apparatus for infusing liquids into the heart in an antegrade direction as defined in claim 27 wherein the pressure conduit further comprises a length of tubing connected to the lumen formed within the external circumference of the hollow member.

29. An apparatus for infusing liquids into the heart in an antegrade direction as defined in claim 28 wherein the second connector comprises a three-way stop cock.

30. An apparatus for infusing liquids into the heart in an antegrade direction as defined in claim 22 further comprising a vent line for venting fluids from the heart, the vent line having first and second ends, the first end opening into the flow lumen and wherein the vent line further comprises a vent connector positioned at the second end.

31. A cannula for administering cardioplegic solutions and other liquids into the heart through the aortic wall, communicating the pressure within the aorta to a remote point, and venting fluids out of the heart, the cannula comprising:

a flow lumen comprising distal and proximal ends and a smooth interior surface adapted to reduce flow turbulence within the flow lumen as liquid flows therethrough, the flow lumen adapted to allow the passage of a liquid from a liquid reservoir to the interior of the heart;

a tapered distal end of the flow lumen, the tapered distal end being adapted for piercing the aortic wall;

a stylet removably locked into the flow lumen and extending out the first end of the flow lumen, the stylet having a sharpened first end;

a connector positioned at the proximal end of the flow lumen and adapted to connect the flow lumen to a liquid reservoir;

a pressure line located substantially parallel to the flow lumen having distal and proximal ends and a diameter smaller than the smallest diameter of the flow lumen;

a pressure port located at the distal end of the pressure line which opens directly into the aorta and outside of the circumference of the flow lumen when the cannula is in place on the aorta and the pressure within the aorta present at the pressure is communicated to the proximal end of the pressure line;

a connector positioned at the proximal end of the pressure line for connecting the second end of the pressure line to a medical device;

a vent line having first and second ends, the first end opening into the flow lumen;

a vent connector positioned at the second end of the vent line; and a suture flange located near the distal end of the flow lumen for securing the cannula to the aortic wall and for limiting the insertion of the cannula into the aortic wall, said suture flange including a tapered ring encircling the flow lumen and adapted for deforming the aortic wall at the site of insertion such that liquid leakage from the aorta is reduced.

* * * * *

UNITED STATES PATENT AND TRADEMARK OFFICE
CERTIFICATE OF CORRECTION

PATENT NO. : 5,013,296

DATED : May 7, 1991

INVENTOR(S) : GERALD D. BUCKBERG et al.

It is certified that error appears in the above-identified patent and that said Letters Patent is hereby corrected as shown below:

```
     Column 1, line 27, after "to" insert --interrupt the normal
operation of the heart.  For obvious--
     Column 2, line 22, after "and" insert --which--
     Column 2, line 24, "stop" should be --stopping--
     Column 3, line 68, "a antegrade" should be --an antegrade--
     Column 4, line 37, "," should be --;--
     Column 5, line 57, delete "22"
     Column 8, line 64, delete first occurrence of "leads"
     Column 9, line 4, "monitor" should be --monitoring--
     Column 9, line 6, "vent" should be --venting--
     Column 11, line 10, "as defined in claim" should be --as defined
in claim 1--
     Column 11, line 55, after "and" insert --is--
```

Signed and Sealed this

Eighth Day of June, 1993

Attest:

MICHAEL K. KIRK

*Attesting Officer*   *Acting Commissioner of Patents and Trademarks*